United States Patent [19]

Sharkey

[11] Patent Number: 4,883,664

[45] Date of Patent: Nov. 28, 1989

[54] MEDICINAL SALVE

[76] Inventor: Mary Sharkey, 80 George Ave., North Adams, Mass. 01247

[21] Appl. No.: 67,806

[22] Filed: Jun. 29, 1987

[51] Int. Cl.$^4$ ..................... A61K 35/78; A61K 31/19; A61K 31/20; A61K 31/125

[52] U.S. Cl. ..................... 424/196.1; 424/DIG. 13; 514/557; 514/558; 514/692; 514/969

[58] Field of Search ......... 424/196.1, 195.1, DIG. 13; 514/969, 557, 558, 692

[56] References Cited

U.S. PATENT DOCUMENTS

| 96,437 | 11/1869 | Jarvis | 424/196.1 |
|---|---|---|---|
| 98,400 | 12/1869 | Oglesbey | 424/196.1 |
| 101,340 | 3/1870 | Wolff | 424/196.1 |
| 224,031 | 2/1880 | Myers | 424/196.1 |
| 381,483 | 4/1888 | Prochowicz | 424/196.1 |

FOREIGN PATENT DOCUMENTS 2058226  7/1971  Fed. Rep. of Germany ... 424/196.1

OTHER PUBLICATIONS

The Merck Index 9th Ed., p. 704, #5207, 1976.

*Primary Examiner*—John W. Rollins
*Attorney, Agent, or Firm*—Fishman, Dionne & Cantor

[57] ABSTRACT

An improved salve having medicinal properties and method of preparing the same, said salve comprising olive oil, beeswax, camphor, pine rosin, and anhydrous lanolin.

2 Claims, No Drawings

MEDICINAL SALVE

BACKGROUND OF THE INVENTION

The present invention relates to an improved slave having medicinal properties, in particular, it relates to a slave for use in treating burns, scalds, etc. to human skin and the like.

In the past, there have been many salves for the topical treatment of human skin. For example, U.S. Pat. No's. 96,437 to Jarvis, 98,400 to Oglesbey, 101,340 to Wolff, 199,684 to Beattie, 224,031 to Myers, and 381,483 to Prochowicz all disclose salves and/or ointments with some claimed medicinal and/or soothing value.

It has been found, however, that most salves or ointments described in the prior art while having medicinal or soothing characteristics do not aid in reducing scaring of the skin tissue. The salve of the present invention not only aids in soothing burnt or scalded skin tissue but also reduces the scaring of said tissue.

Accordingly, it is an object of the present invention to provide a salve having medicinal properties in the treatment of burns, scalds, insect bites and the like.

It is another object of the present invention to provide a salve having medicinal properties which are superior to those of the prior art with regard to the treatment of burns, scalds, insect bites and the like by reducing scaring.

It is a further object of the present invention to provide a method for preparing the salve of the present invention.

The above and other objects and advantages of the present invention will become more apparent after consideration of the following:

DESCRIPTION OF THE PREFERRED EMBODIMENT

The medicinal salve of the present invention is comprised of the following ingredients:
Olive Oil—2 parts by volume
Bee's Wax—1 part by volume
Camphor—1 part by volume
Anhydrous lanolin—4 parts by volume
Pine rosin—a trace In order to produce a medicinal salve having the ingredients listed above, the following method should be employed.

1. To a pyrex cup or similar container add the anhydrous lanolin and melt it over low heat without boiling;
2. Add chopped camphor to melted lanolin under continous heating and melt;
3. Once the camphor has melted, add chopped bee's wax to melted mixture with continuous heating to melt the bee's wax;
4. Add pine rosin to the melted mixture.
5. Once the mixture has been completely melted, remove it from the heating source and allow it to cool slightly.
6. Upon cooling, add olive oil with mixing. The melting mixture is then placed in jars, allowed to cool and coagulate and then the jars are sealed. The salve is now ready for use.

In using the salve on a burnt or scalded portion of human skin or on insect bites or the like, the area to be treated is first cleaned with boric acid. Following the cleaning of the wound, the salve of the present invention is applied to a gauze bandage material large enough to cover the entire burned or scalded area or directly to the wound and bandaged loosely. This regimen is applied three times a day until the wound has healed.

Actual observed treatment as detailed above heals a burn or scald wound and significantly reduces or eliminates scaring.

What is claimed is:

1. A medicinal salve for the topical treatment of burns, scalds, insect bites and the like, said salve comprising 2 parts olive oil by volume, 1 part bee's wax by volume, 1 part camphor by volume, 4 parts anhydrous lanolin by volume a trace of pine rosin.

2. A method of making a salve having medicinal properties comprising melting 1 part by volume of bee's wax, 1 part by volume of camphor, 4 parts by volume of anhydrous lanolin and a trace of pine resin to form a mixture thereof, slightly cooling said mixture, adding 2 parts by volume of olive oil to said slightly cooled mixture and further cooling said mixture to room temperature to form said salve.

* * * * *